United States Patent
Zhang et al.

(10) Patent No.: US 9,622,673 B2
(45) Date of Patent: Apr. 18, 2017

(54) SYSTEM FOR DETERMINING ELECTRICAL STATUS OF PATIENT ATTACHED LEADS

(75) Inventors: Hongxuan Zhang, Schaumburg, IL (US); Ryan Patrick Marry, Des Plaines, IL (US)

(73) Assignee: Siemens Healthcare GmbH (DE)

( * ) Notice: Subject to any disclaimer, the term of this patent is extended or adjusted under 35 U.S.C. 154(b) by 2053 days.

(21) Appl. No.: 12/259,352

(22) Filed: Oct. 28, 2008

(65) Prior Publication Data
US 2009/0157337 A1     Jun. 18, 2009

Related U.S. Application Data

(60) Provisional application No. 61/013,776, filed on Dec. 14, 2007.

(51) Int. Cl.
| A61B 5/0402 | (2006.01) |
| A61B 5/06 | (2006.01) |
| A61B 5/00 | (2006.01) |

(52) U.S. Cl.
CPC ............ *A61B 5/0402* (2013.01); *A61B 5/063* (2013.01); *A61B 5/6843* (2013.01)

(58) Field of Classification Search
CPC ...... A61B 5/0402; A61B 5/6843; A61B 5/063
USPC ........ 702/65, 71, 82, 84, 116; 324/525, 526, 324/756.06, 647, 648, 725; 607/28
See application file for complete search history.

(56) References Cited

U.S. PATENT DOCUMENTS

| | | | |
|---|---|---|---|
| 3,774,592 A * | 11/1973 | Lahr | 600/392 |
| 4,245,643 A * | 1/1981 | Benzing et al. | 607/28 |
| 4,321,932 A | 3/1982 | Francis | |
| 4,577,639 A | 3/1986 | Simon et al. | |
| 4,919,145 A * | 4/1990 | Marriott | 600/536 |
| 4,993,423 A * | 2/1991 | Stice | 600/509 |
| 5,002,064 A | 3/1991 | Allain et al. | |
| 5,201,865 A * | 4/1993 | Kuehn | 607/8 |
| 5,448,997 A | 9/1995 | Kruse et al. | |
| 5,549,646 A * | 8/1996 | Katz et al. | 607/8 |
| 5,788,644 A | 8/1998 | Donehoo et al. | |
| 5,792,194 A * | 8/1998 | Morra | 607/17 |
| 5,921,939 A | 7/1999 | Danielsson et al. | |
| 6,136,008 A * | 10/2000 | Becker et al. | 606/131 |
| 6,516,218 B1 * | 2/2003 | Cheng et al. | 600/509 |
| 6,839,587 B2 | 1/2005 | Yonce | |
| 6,974,420 B2 | 12/2005 | Kaiser et al. | |

(Continued)

*Primary Examiner* — Mischita Henson

(57) ABSTRACT

A system determines electrical status of patient attached leads in medical patient monitoring. The system includes a repository of data indicating multiple predetermined impedance value ranges and corresponding associated lead status information of at least one electrical lead attached to a patient for conducting electrical signals for use in patient monitoring. An impedance measurement processor automatically successively determines whether an impedance value of a particular patient attached lead of multiple electrical leads attached to a patient is within a particular impedance value range of multiple predetermined impedance value ranges. An output processor automatically communicates data comprising a message identifying an electrical status of a particular lead of the multiple electrical leads by deriving status information from the repository in response to a determination the impedance value of the particular patient attached lead is within the particular impedance value range.

13 Claims, 5 Drawing Sheets

(56) References Cited

U.S. PATENT DOCUMENTS

| | | | |
|---|---|---|---|
| 7,047,083 B2 * | 5/2006 | Gunderson et al. | 607/116 |
| 7,245,961 B2 | 7/2007 | Blakley et al. | |
| 2003/0176799 A1 * | 9/2003 | Beatty et al. | 600/509 |
| 2004/0162593 A1 * | 8/2004 | Jorgenson et al. | 607/27 |
| 2005/0288599 A1 * | 12/2005 | MacAdam et al. | 600/509 |
| 2006/0015033 A1 * | 1/2006 | Blakley et al. | 600/509 |
| 2006/0235322 A1 * | 10/2006 | Simske et al. | 600/512 |

* cited by examiner

SYSTEM FOR DETERMINING ELECTRICAL STATUS OF PATIENT ATTACHED LEADS This is a non-provisional application of provisional application Ser. No. 61/013,776 filed Dec. 14, 2007, by H. Zhang et al.

FIELD OF THE INVENTION

This invention concerns a system for determining electrical status of patient attached leads in medical patient monitoring by automatically successively determining whether a lead impedance value is within a particular impedance value range.

BACKGROUND OF THE INVENTION

Coronary artherosclerosis disease (CAD) and heart-related problems are common and often fatal. The principal manifestations of CAD are coronary artherosclerosis (hardening of the coronary arteries) or stenosis (narrowing of the arteries), both of which ultimately cause a reduction in the coronary circulation. A 12-lead electrocardiogram (ECG) is a diagnostic reference standard for evaluating cardiac rhythm and events. A traditional 12-lead ECG system requires 10 electrodes that are strategically placed on the chest and the extremities (nine signal leads and one reference lead). Lead connection failure or partial failure can distort patient activity data and signals, causing incorrect ECG analysis and interpretation, sometimes resulting in late diagnosis and medical care. Compared with total lead connection failure, partial lead connection or sensor failures in patient signal acquisition may not be easily recognized and detected in clinical applications. A partial lead connection failure may be indicated by high impedance.

Known lead failure detection methods, including DC (pull up and pull down) and AC (active lead detection) methods fail to quantify and characterize an impedance measurement. One known lead failure analysis system utilizes a DC mode to measure lead connection impedance and employs voltage pull up or pull down elements for detection of a lead failure event. However this system does not work well for detection of a partial lead connection failure or high impedance connection. Additionally, reference lead (e.g., a right leg connection) failure affects remaining ECG leads, resulting in a low quality cardiac signal on the leads, and lead complexity and difficulty in lead failure mapping and compensation. Known lead failure analysis systems may also use an AC signal to detect and analyze lead connection status by sending a small AC stimulating signal (e.g., to a reference lead) and verifying a feedback response signal on individual ECG leads. The AC lead connection detection system operates in an active mode and involves sending AC stimulation signals to a patient body which presents an additional risk and safety impairment and contributes noise and artifacts to patient signals.

Known lead connection test and detection systems, both passive (DC) and active (AC), fail to successfully measure, verify and characterize detailed status information of a lead connection on a patient, such as a partial connection failure and high impedance connection. Further, known DC or AC based cardiac lead failure detection systems typically employ an additional circuit for cardiac signal sensing, conditioning, amplitude comparison and stimulation signal generation increasing system complexity and cost. A system according to invention principles addresses these deficiencies and related problems.

SUMMARY OF THE INVENTION

A system includes a controllable impedance bridge to analyze, quantify and characterize a patient signal acquired from cardiac leads and sensors and to determine a lead connection impedance range. A system determines electrical status of patient attached leads in medical patient monitoring. The system includes a repository of data indicating multiple predetermined impedance value ranges and corresponding associated lead status information of at least one electrical lead attached to a patient for conducting electrical signals for use in patient monitoring. An impedance measurement processor automatically successively determines whether an impedance value of a particular patient attached lead of multiple electrical leads attached to a patient is within a particular impedance value range of multiple predetermined impedance value ranges. An output processor automatically communicates data comprising a message identifying an electrical status of a particular lead of the multiple electrical leads by deriving status information from the repository in response to a determination the impedance value of the particular patient attached lead is within the particular impedance value range.

DETAILED DESCRIPTION OF THE INVENTION

Figure 1:
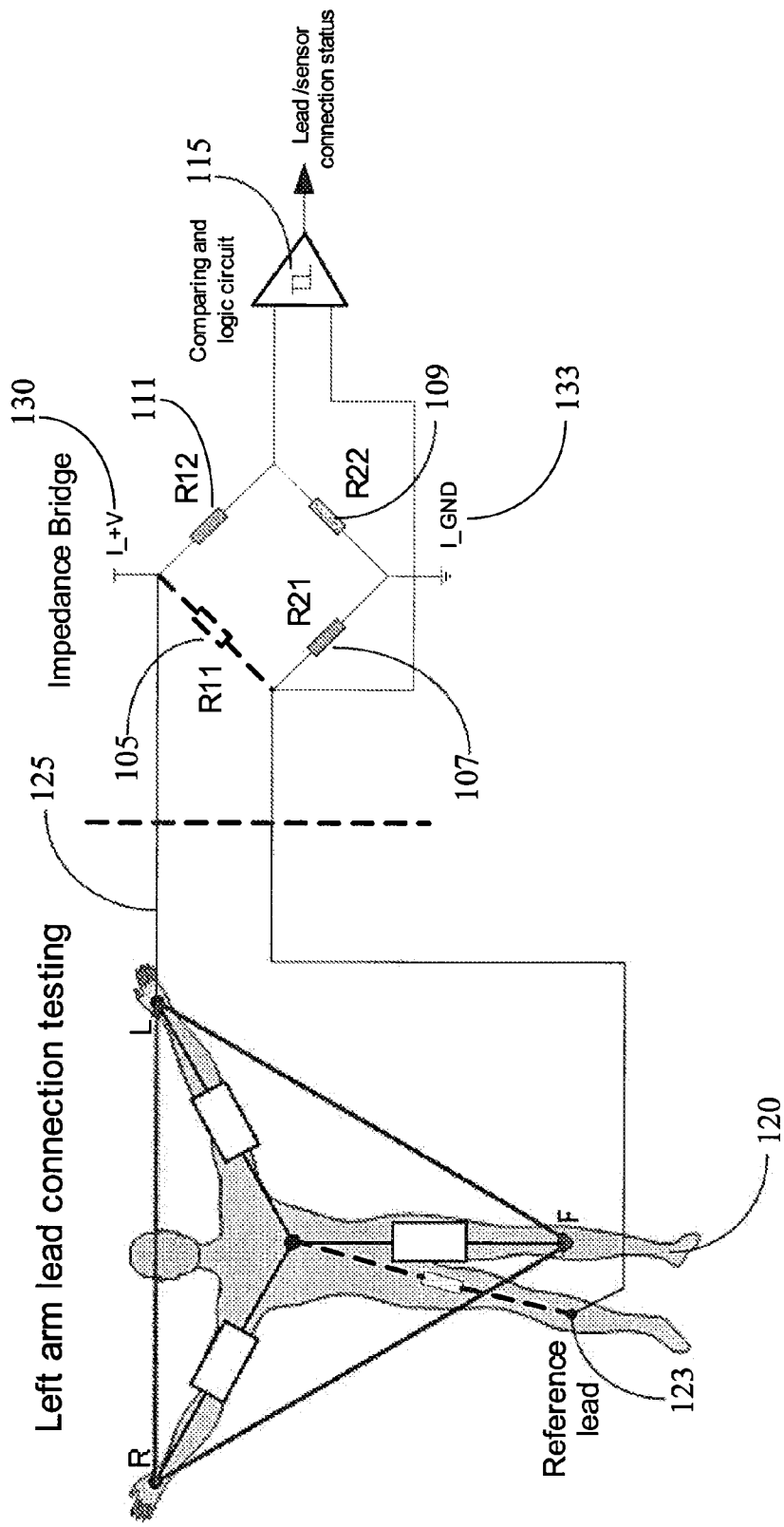
FIG. 1 shows a system for determining electrical status of patient attached leads in medical patient monitoring using impedance bridge based lead and sensor connection detection, according to invention principles.

The detection and characterization of electrical status of a patient attached lead connection aids patient monitoring, health evaluation and medical treatment. Lead and sensor partial connections and connection failures occur frequently in medical monitoring. However, known lead detection systems fail to successfully locate, characterize and quantify partial lead failures. A system according to invention principles performs lead and sensor operational status testing and verification with sensitivity and reliability enabling accurate and precise patient monitoring and medical treatment. The system verifies stable and reliable lead connections for patient signal monitoring, data recording and analysis of cardiac signals of surface ECG and intra-cardiac electrophysiological activities, for example. Surface electrical connections of electrodes and sensors are monitored and checked continuously to ensure the quality of a surface ECG signal obtained from a patient. The system provides detailed characterization of cardiac lead connections, such as partial connection failure (high impedance of an ECG lead connection) ensuring patient signal precision. The system includes a controllable impedance bridge module for analyzing, characterizing and quantifying a patient signal acquired from cardiac leads and sensors. In cardiac lead connection status investigation, the system characterizes signals by impedance bridge based lead and sensor connection failure detection and warning generation. The system detects a partial lead connection and performs a patient impedance analysis and connection evaluation and categorization using automatic and adaptive lead switching and compensation. Furthermore, the patient impedance monitoring and characterization may be employed in patient health analysis and diagnosis, such as for determining low heart blood flow (myocardial ischemia) based on an increasing corresponding patient impedance.

The system employs a versatile impedance bridge for identifying lead failure, partial lead failure, and lead connection impedance status. Clinically, detailed information of a lead connection provides early warning and interpretation of patient signals, such as signals from a failing lead or partially connected lead. An electrode impedance bridge balancing method provides status mapping for a real-time application, operating in both a unipolar and a bipolar mode. The system performs precise patient impedance measurement and characterization for construction of a multi-dimensional resistance and impedance map for patient health monitoring and disease diagnosis. The system provides automatic real time lead connection status detection and analysis reduces cost of medical diagnosis and treatment, and improves sensitivity, stability and reliability of a corresponding clinical application used for medical signal processing. The system also performs signal lead impedance range testing and characterization and categorizes partial lead failure and connection status.

The impedance bridge does not require an additional stimulation signal for lead failure detection (such as an AC active mode for connection detection). This eliminates a further source of potential patient safety impairment. The system employs passive lead failure detection that decreases signal distortion effects from noise and artifacts. The system uses an electrode lead impedance bridge balancing method for lead connection characterization (impedance range categorization), such as 1 for good connection, 0.5 for poor connection, and 0 for connection failure, for example. The system uses impedance matching to measure, detect and diagnose impedance of patient attached leads for patient health evaluation and suitable medical treatment. The electrode impedance analysis and diagnosis determined by bridge balancing is used for surface ECG signals, electrophysiological activities and hemodynamic signals, such as intra-cardiac electrograms (ICEG) signals and invasive blood pressure signals, for example. The electrode impedance bridge balancing method does not require extra power for bridge balancing and does not introduce additional complexity in the impedance bridge electronics and hardware. The electrode impedance bridge balancing is usable independently for each lead connection and is used to compensate for lead failure by automatically initiating lead signal prediction in response to failure detection. For example, if lead I is partially failed, lead II and Lead III signals are adaptively utilized to compensate for the signal quality loss on lead I. The lead connection diagnosis and compensation determination function may be implemented in logic firmware or software in the system.

Additionally, during lead connection monitoring and analysis, individual patient electrode lead impedance is determined and used for qualitative and quantitative diagnosis and characterization of patient cardiac function. The impedance distribution on different leads and cardiac electrophysiological vectors is captured and mapped to localize and diagnose cardiac tissue regions and functions. For example, myocardial ischemia and infarction information is tracked by patient impedance analysis and mapping. Beside cardiac signal and data acquisition, medical treatment of cardiac disease also needs accurate and precise cardiac signal information (signals with high quality having high signal to noise ratio) including ECG signal amplitude and waveform shape information, for example.

Impedance as used herein is a measure of the degree to which a component resists the flow of electrical current if a given voltage is applied and if a real quantity is measured in ohms. A processor as used herein is a device for executing stored machine-readable instructions for performing tasks and may comprise any one or combination of, hardware and firmware. A processor may also comprise memory storing machine-readable instructions executable for performing tasks. A processor acts upon information by manipulating, analyzing, modifying, converting or transmitting information for use by an executable procedure or an information device, and/or by routing the information to an output device. A processor may use or comprise the capabilities of a controller or microprocessor, for example. A processor may be electrically coupled with any other processor enabling interaction and/or communication there-between. A processor comprising executable instructions may be electrically coupled by being within stored executable instruction enabling interaction and/or communication with executable instructions comprising another processor. A user interface processor or generator is a known element comprising electronic circuitry or software or a combination of both for generating display images or portions thereof. A user interface comprises one or more display images enabling user interaction with a processor or other device.

An executable application comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters. A user interface (UI), as used herein, comprises one or more display images, generated by a user interface processor and enabling user interaction with a processor or other device and associated data acquisition and processing functions.

The UI also includes an executable procedure or executable application. The executable procedure or executable application conditions the user interface processor to generate signals representing the UI display images. These signals are supplied to a display device which displays the image for viewing by the user. The executable procedure or executable application further receives signals from user input devices, such as a keyboard, mouse, light pen, touch screen or any other means allowing a user to provide data to a processor. The processor, under control of an executable procedure or executable application, manipulates the UI display images in response to signals received from the input devices. In this way, the user interacts with the display image using the input devices, enabling user interaction with the processor or other device. The functions and process steps herein may be performed automatically or wholly or partially in response to user command. An activity (including a step) performed automatically is performed in response to executable instruction or device operation without user direct initiation of the activity. An object or data object comprises a grouping of data, executable instructions or a combination of both or an executable procedure.

FIG. 1 shows a system for determining electrical status of patient attached leads in medical patient monitoring using impedance bridge based lead and sensor connection detection. Sensor and lead connectivity status are important factors in providing accurate diagnosis and interpretation of monitoring signals and data. FIG. 1 shows a basic configuration for lead failure detection of a surface ECG signal, for example. Electrode lead connection impedance (including patient impedance and lead and sensor impedance) is one balance component R11 (105) in the impedance bridge including R12 (111), R21 (107), and R22 (109) balancing impedance components, which are individually tunable and adjustable for different situations and patients (including different patient skin types).

In the system, typically the electrode lead signals and voltage potentials are acquired with reference to a right leg reference electrode lead 123 (a typical clinical floating ground reference) of patient 120. The impedance bridge is constructed between an individual electrode lead 125 and reference electrode lead 123, in which R11 (105) represents connection and patient impedance of lead 125 relative to lead 123 and R12, R21, R22 are bridge balancing impedances. Isolated power (I_+V 130) and isolated ground (I_GND 133) are used for patient safety in case of high voltage fibrillation, for example. The system automatically tunes and adjusts bridge impedance and determines an impedance range of R11 (105). In one embodiment, if the determined impedance range of R11 (105) lies outside of a normal value range, and is higher than 10 kΩ, for example, comparator and logic circuit 115 outputs a message signal indicating lead failure. If the determined impedance range of R11 (105) lies within a reasonable range such as <10 kΩ (typically patient body impedance is around 600 Ω to 5-6 kΩ including reasonable lead connection impedance), the impedance bridge and comparator 115 does not output a warning message signal. However, if the determined impedance range of R11 (105) is determined to be infinite or higher than a normal range, indicating a poor electrical connection, the impedance bridge and comparator 115 sends a message signal indicating lead failure and alerts the monitoring system and users.

Figure 2:
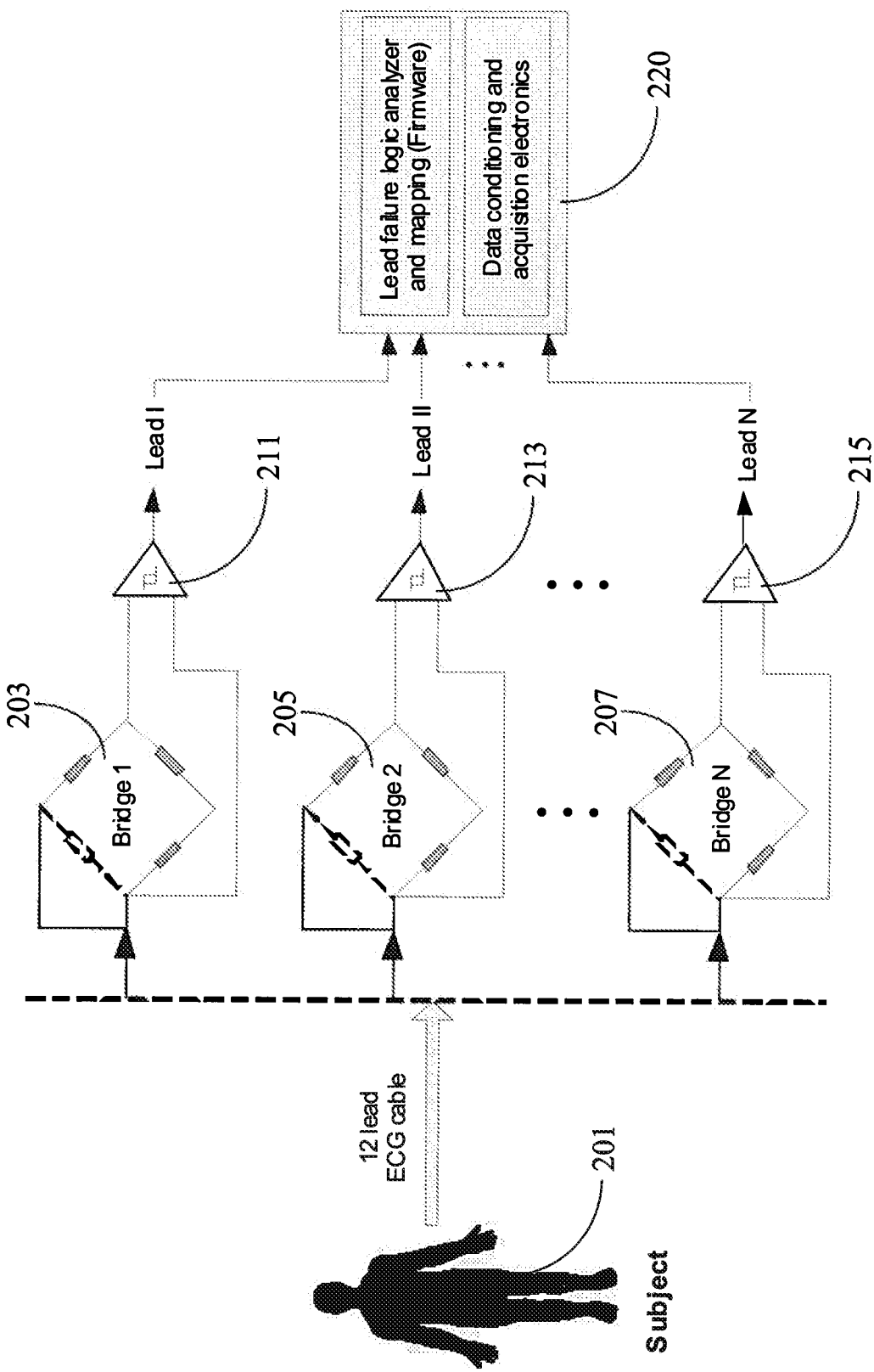
FIG. 2 shows a connection detection system for a multi-lead/multi-channel sensor arrangement, according to invention principles.

FIG. 2 shows a lead connection failure detection system for a multi-lead/multi-channel sensor arrangement indicating multiple electrode lead connections of a lead surface ECG system, for example. Lead/sensor detection Impedance Bridges 203, 205-207 of individual leads attached to patient 201 are independent and provide multi-channel lead status information for analysis and mapping by the system. Corresponding comparators 211, 213-215 send signals indicating lead status and failure to data analysis and processing unit 220. Lead status and failure analysis and processing unit 220 may be implemented in separate circuitry or may be integrated into existing data conditioning and acquisition interface and processing electronic circuitry. Additionally, lead status and failure analysis and processing unit 220 provides an electrode lead signal compensation and prediction function. For example, if lead I sensor or connection failed, lead II and lead III can be utilized to reconstruct a lead I virtual signal for the patient. The system also sends lead I connection failure information to a device, e.g., a display for presentation to a user. Similarly, if an ECG chest lead has a failed connection, for example, so that no signal is coming from a V2 or V3 lead, the signals of the rest of the ECG chest leads are used to reconstruct the signal from V2 or V3, using a weighted signal combination, such as the following:

$$V2 = \frac{\sum \alpha_n \cdot \text{signal\_Lead}_n}{5}, \text{ in which } \sum \alpha_n = 1$$

Lead status and failure data analysis and processing unit 220 analyzes and maps lead status data to data indicating potential patient medical conditions supporting physician diagnosis. The lead failure feedback data is used to automatically initiate generation of a virtual reconstructed ECG lead signal for communication to a patient monitoring system and user.

Figure 3:
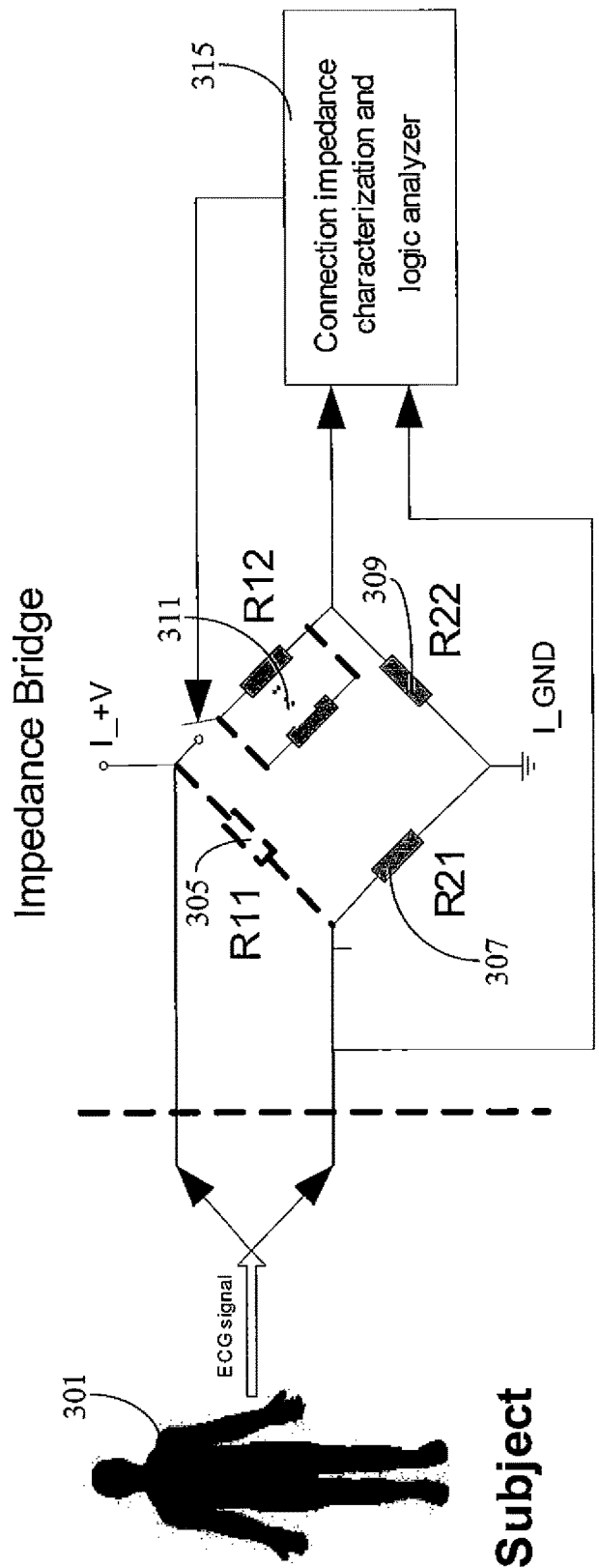
FIG. 3 shows a system for impedance range testing and verification of patient attached lead and sensor connection electrical status, according to invention principles.

FIG. 3 shows a system for impedance range testing and verification of patient 301 attached lead and sensor connection electrical status. Complete lead or sensor failure is usually easily recognized and verified by medical doctors and technicians. However, partial clinical lead or sensor connection failures involving high lead connection impedance, for example, cannot readily be recognized and quantified visually or by general methods. Additionally, partial lead and sensor failures can cause poor patient signal quality, and introduce additional on-off connection noise and artifacts, which may cause distortion in data acquisition and inaccurate diagnosis and interpretation of patient health and status. The system performs impedance testing and measurement and automatically compares measured lead impedance with a normal connection impedance range for lead failure characterization. For example, the impedance bridge arrangement of FIG. 3 performs impedance range testing, verification of lead and sensor connection and impedance categorization. The lead connection impedance range analysis enables patient signal quality to be characterized in more detail.

In the Figure, R11 (305) is electrode lead connection impedance and R12 (311) is a balancing impedance which is controlled and adjusted by impedance and logic analyzer 315. The impedance bridge comprises R11 (305), R12 (311), R21 (307), and R22 (309). The system determines a lead connection impedance range, for example, an impedance less than 6 kΩ indicates a good lead connection, an impedance between 6 kΩ and 20 kΩ indicates an intermediate connection, an impedance between 20 kΩ and infinite impedance indicates a poor lead and sensor connection and an infinite impedance value indicates complete lead connection failure. The impedance bridge utilizes multi-impedance balance arm R12 (311) to determine an impedance range encompassing impedance of R11 (305) and to indicate whether the range indicates partial lead connection failure.

Figure 4:
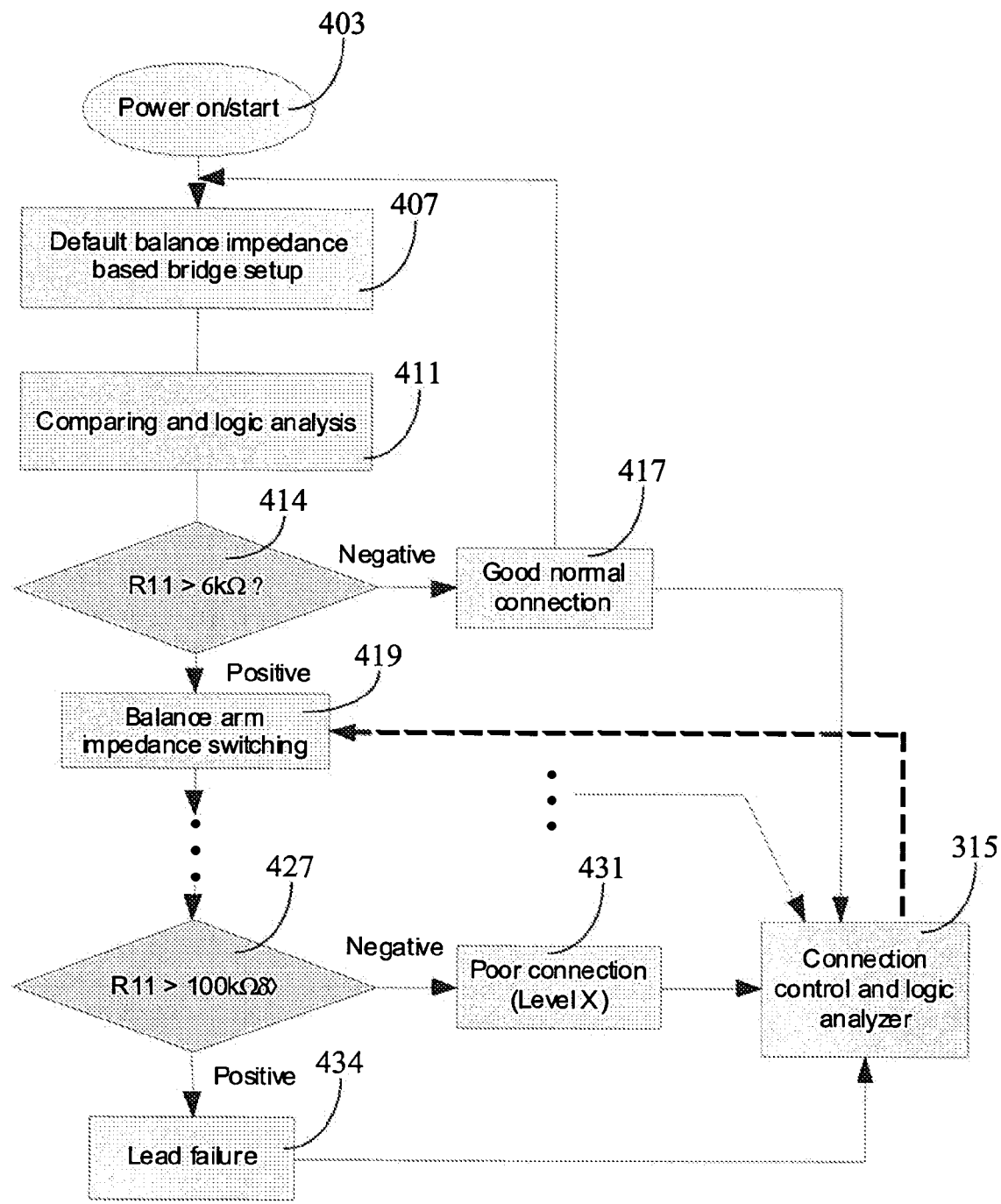
FIG. 4 shows a flowchart of a process for lead and sensor connection measurement, detection and diagnosis with multi-range impedance capability, according to invention principles.

FIG. 4 shows a flowchart of a process employed by the impedance bridge system of FIG. 3 for lead and sensor connection measurement, detection and diagnosis with multi-range impedance capability. The system integrates partial lead and sensor connection failure impedance range measurement with lead failure detection. Following power-on in step 403, connection impedance and logic analyzer 315 in step 407 controls the impedance balance arm and initially selects a default R12 (311) value, for example 6 kΩ. If the impedance bridge comparison in step 411 provides a Negative output value in step 414 indicating low connection impedance, the lead connection indicating good condition in step 417 is provided to impedance and logic analyzer 315 and the process returns to the start. Otherwise, if the output of the bridge is positive, this indicates the lead connection is abnormal and connection impedance and logic analyzer 315 in step 419 automatically switches impedance R12 (311) to compare R11 (305) with a 20 kΩ balance impedance, for example. If the balance arm impedance is 20 kΩ and the bridge circuit output is negative, this indicates an intermediate connection and the input (lead connection) impedance is between 6 kΩ and 20 kΩ. Connection impedance and logic analyzer 315 initiates switching and multi-value impedance range testing using range transition thresholds including, a 6 kΩ threshold below which is a normal connection, a 20 kΩ threshold below which is a poor/intermediate connection, a 100 kΩ threshold below which is a poor lead connection and above which is a complete connection failure or open lead, for example. If the impedance bridge comparison provides a Negative output value in step 427 because R11 (305) is between 20 kΩ and 100 kΩ, data indicating a poor lead connection in step 431 is provided to impedance and logic analyzer 315. If the impedance bridge comparison provides a Positive output value in step 427 because R11 (305) exceeds 100 kΩ, data indicating a lead failure in step 434 is provided to impedance and logic analyzer 315.

The system automatically measures and detects a lead connection impedance range and lead connection failure and also automatically provides lead signal prediction compensation using data from other ECG leads in response to detection of a defective lead connection. In response to a determination that a lead, such as lead I, is in poor connection condition, lead status and warning information is communicated to connection and logic analyzer 315. Analyzer 315 determines if the signal from lead I is still usable or is of poor signal quality. Based on the determination, connection and logic analyzer 315 automatically adaptively controls lead switching to determine if connections of leads to be used in the prediction are good and initiates lead voltage prediction. Further, warning message and predicted (virtual) lead information is communicated to a user and patient monitoring system. In another embodiment, automated lead switching and lead voltage prediction to replace the failed lead or partial failed lead employs signal weight adjustment for virtual lead construction using one of a variety of different kinds of method, such as using an artificial neural network or fuzzy signal weight analysis, for example. This is done to optimize predicted signal quality of the reconstructed lead.

The system lead connection impedance measurements are used for both unipolar and bipolar signals. The signal or impedance testing, verification and range testing may be implemented between signals (including between a signal and patient reference), and between a signal and GND (instrumentation isolated ground reference). The system lead connection impedance measurement and diagnosis quantifies and characterizes the patient body and electrical conduction impedance. For example, a Lead I signal is the differential signal between left arm and right arm, the differential impedance is usually between 500Ω to 6 kΩ as working guidance for impedance measurement and patient disease characterization and diagnosis. For example, during myocardial ischemia and infarction cases, blood flow is slowed down and the corresponding patient anatomical region impedance increases. The system automatically advantageously measures variance of the patient anatomical impedance in order to detect patient ischemia earlier for diagnosis and on-time medical treatment.

The system lead connection impedance measurements may be utilized for different medical applications, such as intra-cardiac impedance and capacitance characterization to facilitate locating and diagnosing intra-cardiac disease, such as atrial fibrillation or ventricle tachycardia, for example. The system is also usable in hemodynamic applications and integrates electrophysiological measurements and hemodynamic analysis to produce an accurate clinical diagnosis. The system may be implemented using software mapping and virtual impedance bridge construction by deriving impedance by calculation from voltage and current of signals and leads. Impedance function mapping is used for lead connection monitoring and characterization and may be used to study patient body and tissue impedance and functions.

Figure 5:
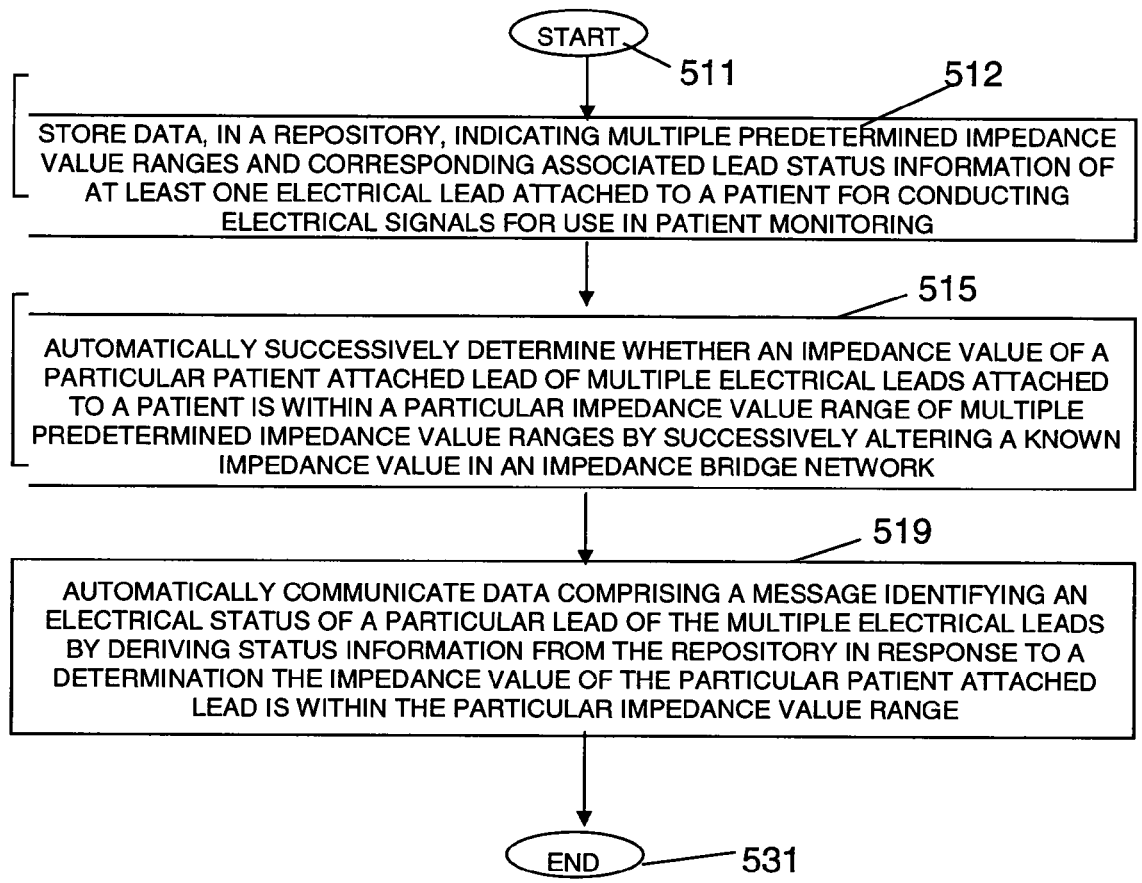
FIG. 5 shows a flowchart of a process used by a system for determining electrical status of patient attached leads in medical patient monitoring using impedance bridge based lead and sensor connection detection, according to invention principles.

FIG. 5 shows a flowchart of a process used by a system for determining electrical status of patient attached leads in medical patient monitoring using impedance bridge based lead and sensor connection detection. In step 512, following the start at step 511, the system of FIG. 3 stores data in a repository of data in unit 315 indicating multiple predetermined impedance value ranges and corresponding associated lead status information of at least one electrical lead attached to a patient for conducting electrical signals for use in patient monitoring. The repository of data comprises stored data in electrical memory. In one embodiment the repository of data comprises data stored in an arrangement of electrical components. In step 515 an impedance measurement processor in unit 315 automatically successively determines whether an impedance value of a particular patient attached lead of multiple electrical leads attached to a patient is within a particular impedance value range of multiple predetermined impedance value ranges by successively altering a known impedance value in an impedance bridge network. The impedance measurement processor automatically determines impedance value ranges of the multiple electrical leads attached to the patient. The particular impedance value and range is resistive and the impedance measurement processor applies DC voltage to the impedance bridge network in successively altering a known impedance value in the impedance bridge network to determine the particular impedance value range. In another embodiment, the particular impedance value and range is reactive and comprises complex number values and the impedance measurement processor applies AC voltage to the impedance bridge network in successively altering a known impedance value in the impedance bridge network to determine the particular impedance value range.

The multiple predetermined impedance value ranges include at least two of, (a) a first value range indicating a particular patient attached lead has an acceptable connection, (b) a second value range indicating a particular patient attached lead has a poor or intermediate connection and (c) a third value range indicating a particular patient attached lead has negligible connection. The first value range is below a threshold of approximately 4-7 kOhms, the second value range exceeds the first value range but is below approximately 18-22 kOhms and the third value range exceeds the second value range. The multiple predetermined impedance value ranges include a fourth value range indicating a particular patient attached lead exceeds approximately 100 kOhms and is a failed connection. Further, the impedance measurement processor automatically initiates prediction of a lead signal conveyed on the particular patient attached lead in response to a determination the particular impedance value range of the particular patient attached lead indicates an unacceptable connection.

In step 519 an output processor in unit 315 automatically communicates data comprising a message identifying an electrical status of a particular lead of the multiple electrical leads, as well as messages identifying electrical status of the multiple electrical leads, by deriving status information from the repository in response to a determination the impedance value of the particular patient attached lead is within the particular impedance value range. A message identifies electrical status of the particular patient attached lead is unacceptable and inhibits processing of signal data conveyed on the particular patient attached lead in response to determining an impedance value of the particular patient attached lead is within a particular impedance value range. Further, the data comprising the message is automatically communicated for display on a monitor of a patient monitoring device. The process of FIG. 5 terminates at step 531.

The systems and processes of FIGS. 1-5 are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. The system detects, analyzes, characterizes and categorizes lead and sensor connections including partial connections and failed connections and automatically and adaptively switches between patient leads, supports diagnosis and predicts output of a failed lead. The processes and applications may, in alternative embodiments, be located on one or more (e.g., distributed) processing devices accessing a network linking the elements of FIG. 1. Further, any of the functions and steps provided in FIGS. 1-5 may be implemented in hardware, software or a combination of both and may reside on one or more processing devices located at any location of a network linking the elements of FIG. 1 or another linked network, including the Internet.

What is claimed is:

1. A system for determining electrical status of patient attached leads in medical patient monitoring, comprising:

a repository of data indicating a plurality of predetermined impedance value ranges and corresponding associated lead status information of at least one electrical lead attached to a patient for conducting electrical signals for use in patient monitoring;

an impedance measurement processor using a substantially passive impedance bridge network operating exclusive of constant current injection for automatically successively determining whether an impedance value of a particular patient attached lead of a plurality of electrical leads attached to patient skin is within a particular impedance value range of a plurality of predetermined impedance value ranges and capturing a cardiac impedance distribution together with electrophysiological vectors on different leads for together mapping to localize cardiac tissue conditions and indicating a potential patient medical condition supporting diagnosis, said impedance measurement processor predicts a lead signal voltage conveyed on said particular patient attached lead using remaining acceptable lead signals in response to a determination said particular impedance value range of said particular patient attached lead indicates an unacceptable connection and comprises a failed lead, wherein said prediction of said lead signal conveyed on said particular patient attached lead is in response to a weighted lead signal combination using remaining said acceptable lead signals; and an output processor for communicating data comprising a message identifying an electrical status of a particular lead of said plurality of electrical leads by deriving status information from said repository in response to a determination said impedance value of said particular patient attached lead is within said particular impedance value range.

2. A system according to claim 1, wherein
said repository of data comprises stored data in electrical memory and
said impedance measurement processor automatically determines whether an impedance value of a particular patient attached lead indicates a potential patient medical condition supporting diagnosis and captures ECG signal amplitude and waveform shape information.

3. A system according to claim 1, wherein
said repository of data comprises data stored in an arrangement of electrical components,
said plurality of predetermined impedance value ranges indicate potential patient medical conditions and
said impedance measurement processor automatically selects between a potential patient medical condition and an unacceptable connection based on an impedance value of a particular patient attached lead.

4. A system according to claim 1, wherein
said plurality of predetermined impedance value ranges include, (a) a first value range indicating a particular patient attached lead has an acceptable connection, (b) a second value range indicating a particular patient attached lead has a poor or intermediate connection and (c) a third value range indicating a particular patient attached lead has negligible connection.

5. A system according to claim 4, wherein
said first value range is below a threshold of approximately 4-7 kOhms,
said second value range exceeds said first value range but is below approximately 18-22 kOhms and
said third value range exceeds said second value range.

6. A system according to claim 4, wherein
said plurality of predetermined impedance value ranges include a fourth value range indicating a particular patient attached lead exceeds approximately 100 kOhms and is a failed connection.

7. A system according to claim 1, wherein
said output processor automatically communicates data comprising at least one message identifying electrical status of said particular patient attached lead is unacceptable and inhibits processing of signal data conveyed on said particular patient attached lead in response to determining an impedance value of said particular patient attached lead is within a particular impedance value range.

8. A system according to claim 1, wherein
said impedance measurement processor automatically determines impedance value ranges of said plurality of electrical leads attached to said patient and
said output processor automatically communicates data comprising at least one message identifying electrical status of said plurality of electrical leads.

9. A system according to claim 1, wherein
said output processor automatically communicates said data comprising said message for display on a monitor of a patient monitoring device.

10. A system for determining electrical status of patient attached leads in medical patient monitoring, comprising:
a repository of data indicating a plurality of predetermined impedance value ranges and corresponding associated lead status information of at least one electrical lead attached to a patient for conducting electrical signals for use in patient monitoring, said plurality of predetermined impedance value ranges indicating potential patient medical conditions;
an impedance measurement processor using a substantially passive impedance bridge network operating exclusive of constant current injection for automatically successively determining whether an impedance value of a particular patient attached lead of a plurality of electrical leads attached to patient skin is within a particular impedance value range of a plurality of predetermined impedance value ranges by successively altering a known impedance value in an impedance bridge network and said impedance measurement processor automatically determines between whether an impedance value of a particular patient attached lead indicates a potential patient medical condition supporting diagnosis or an unacceptable connection and captures a cardiac impedance distribution together with electrophysiological vectors on different leads for mapping to localize cardiac tissue conditions and indicating a potential patient medical condition supporting diagnosis, wherein said impedance measurement processor automatically initiates prediction of a lead signal voltage conveyed on said particular patient attached lead in response to a weighted lead signal combination using remaining acceptable lead signals; and
an output processor for automatically communicating data comprising a message identifying an electrical status of a particular lead of said plurality of electrical leads by deriving status information from said repository in response to a determination said impedance value of said particular patient attached lead is within said particular impedance value range.

11. A system according to claim 10, wherein
said impedance measurement processor automatically initiates said prediction of said lead signal voltage conveyed on said particular patient attached lead using said remaining acceptable lead signals in response to a determination said particular impedance value range of said particular patient attached lead indicates an unacceptable connection,
said particular impedance value and range is resistive and
said impedance measurement processor applies DC voltage to said impedance bridge network in successively altering a known impedance value in said impedance bridge network to determine said particular impedance value range.

12. A system according to claim 10, wherein
said particular impedance value and range is reactive and comprises complex number values and
said impedance measurement processor applies AC voltage to said impedance bridge network in successively altering a known impedance value in said impedance bridge network to determine said particular impedance value range.

13. A method for determining electrical status of patient attached leads in medical patient monitoring, comprising the activities of:
employing at least one processing device for,
storing in a repository, data indicating a plurality of predetermined impedance value ranges and corresponding associated lead status information of at least one electrical lead attached to a patient for conducting electrical signals for use in patient monitoring;
using a substantially passive impedance bridge network operating exclusive of constant current injection for automatically successively determining whether an impedance value of a particular patient attached lead of a plurality of electrical leads attached to patient skin is within a particular impedance value range of a plurality of predetermined impedance value ranges and indicates a potential patient medical condition supporting diagnosis;
capturing a cardiac impedance distribution together with electrophysiological vectors on different leads for mapping to localize cardiac tissue conditions and indicating a potential patient medical condition supporting diagnosis;
predicting a lead signal conveyed on said particular patient attached lead using remaining acceptable lead signals in response to a determination said particular impedance value range of said particular patient attached lead indicates an unacceptable connection, wherein said prediction of said lead signal conveyed on said particular patient attached lead is in response to a weighted lead signal combination using remaining said acceptable lead signals; and
communicating data comprising a message identifying an electrical status of a particular lead of said plurality of electrical leads by deriving status information from said repository in response to a determination said impedance value of said particular patient attached lead is within said particular impedance value range.

* * * * *